United States Patent

Wang et al.

[11] Patent Number: 5,977,138
[45] Date of Patent: Nov. 2, 1999

[54] ETHER MUSCARINIC ANTAGONISTS

[75] Inventors: Yuguang Wang, North Brunswick; Wei K. Chang, Livingston; Sundeep Dugar, Bridgewater; Samuel Chackalamannil, East Brunswick, all of N.J.

[73] Assignee: Schering Corporation, Kenilworth, N.J.

[21] Appl. No.: 08/910,616

[22] Filed: Aug. 13, 1997

Related U.S. Application Data

[60] Provisional application No. 60/024,112, Aug. 15, 1996.

[51] Int. Cl.$^6$ ...................... A61K 31/445; C07D 401/04
[52] U.S. Cl. ........................... 514/316; 546/187; 546/188
[58] Field of Search .................................. 546/187, 188; 514/320, 316

[56] References Cited

U.S. PATENT DOCUMENTS

| | | | |
|---|---|---|---|
| 3,260,723 | 7/1966 | L'Italien et al. | 260/294.7 |
| 5,100,901 | 3/1992 | Sugimoto et al. | 514/319 |
| 5,580,883 | 12/1996 | Goto et al. | 514/315 |
| 5,652,242 | 7/1997 | Wayne et al. | 514/255 |

FOREIGN PATENT DOCUMENTS

| | | |
|---|---|---|
| 0 229 391 | 7/1987 | European Pat. Off. . |
| 449195 | 10/1991 | European Pat. Off. . |
| 478363 | 4/1992 | European Pat. Off. . |
| 540051 | 5/1993 | European Pat. Off. . |
| 635505 | 1/1995 | European Pat. Off. . |
| 4202185 | 7/1992 | Japan . |
| WO 96/26196 | 8/1996 | WIPO . |

OTHER PUBLICATIONS

Baumgold et al, *Eur. J. Pharmacol.*, 251 (1994), pp. 315–317.
Melchiorre et al, *J. Med. Chem.*, 36 (1993), pp. 3734–3737.
Logemann et al, Brit. J. Pharmacol., 17 (1961), pp. 286–296.
Cheng et al, *Biochem. Pharmacol.*, 22 (1973), pp. 3099–3108.
Watson et al, *J. Pharmacol. Exp. Ther.*, 237 (1986), pp. 411–418.
Sindelar, et al., *Collect. Czech Chem. Commun.*, 54 (8) (1989), pp. 2240–2247.
Parnetti, L., *Clinical Pharmacokinetics*, 29 (2) (1995), pp. 110–129, abstract only.

*Primary Examiner*—Alan L. Rotman
*Assistant Examiner*—Charanjit S Aulakh
*Attorney, Agent, or Firm*—Anita W. Magatti

[57] ABSTRACT 1,4 Di-substituted piperidine muscarinic antagonists of formula I

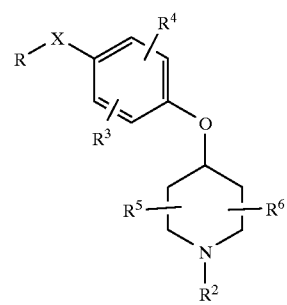

or an isomer, pharmaceutically acceptable salt, ester or solvate thereof, wherein X is a bond, —O—, —S—, —SO—, —SO$_2$—, —CO—, —C(OR$^7$)$_2$—, —CH$_2$—O—, —O— CH$_2$—, —CH=CH—, —CH$_2$—, —CH(C$_1$-C$_6$ alkyl)-, —C(C$_1$-C$_6$ alkyl)$_2$—, —CONR$^{17}$—, —NR$^{17}$CO—, —O—C(O)NR$^{17}$—, —NR$^{17}$C(O)—O—, —SO$_2$NR$^{17}$— or —NR$^{17}$SO$_2$—;

R is cycloalkyl, optionally substituted phenyl or optionally substituted pyridyl;

R$^2$ is H, alkyl, optionally substituted cycloalkyl, cycloalkenyl, t-butoxycarbonyl or optionally substituted piperidinyl; and the remaining variables are as defined in the specification, are disclosed. Compounds of formula I are useful for treating cognitive disorders such as Alzheimer's disease. Also disclosed are pharmaceutical compositions, methods of preparation and combinations of compounds of formula I with ACh'ase inhibitors.

19 Claims, No Drawings

ETHER MUSCARINIC ANTAGONISTS

This appication is a Provisional application Ser. No. 60/024,112, filed on Aug. 15, 1996.

BACKGROUND OF THE INVENTION

The present invention relates to 1,4-di-substituted piperidines, wherein the 4-position substituent is attached through an ether linkage, which compounds are useful in the treatment of cognitive disorders, pharmaceutical compositions containing the compounds, methods of treatment using the compounds, and to the use of said compounds in combination with acetyicholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective m2 muscarinic antagonist.

The present invention relates to a class of 1,4-di-substituted piperidines, some of which have m2 selectivity even higher than that of 3-α-chloroimperialine. Logemann et al (Brit. J. Pharmacol. (1961), 17, 286–296) describe certain di-N-substituted piperazines, but these are different from the inventive compounds of the present invention. Furthermore, the compounds of Logemann et al. are not disclosed to have activity against cognitive disorders.

SUMMARY OF THE INVENTION

The present invention relates to compounds according to the structural formula I,

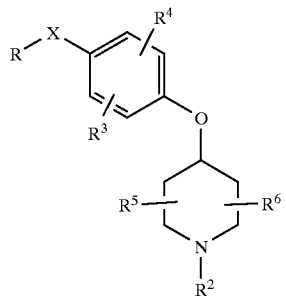

I or an isomer, pharmaceutically acceptable salt, ester or solvate thereof, wherein X is a bond, —O—, —S—, —SO—, —SO$_2$—, —CO—, —C(OR$^7$)$_2$—, —CH$_2$—O—, —O— CH$_2$—, —CH=CH—, —CH$_2$—, —CH(C$_1$-C$_6$ alkyl)-, —C(C$_1$-C$_6$ alkyl)$_2$-, —CONR$^{17}$—, —NR$^{17}$CO—, —O—C(O)NR$^{17}$—, —NR$^{17}$C(O)—O—, —SO$_2$NR$^{17}$— or —NR$^{17}$SO$_2$—;

R is C$_3$–C$_6$ cycloalkyl,

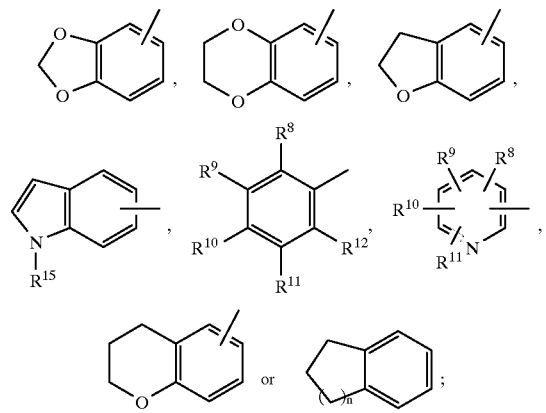

n is 1, 2 or 3;

R$^2$ is H, C$_2$–C$_7$ alkyl, C$_3$–C$_7$ cycloalkyl, C$_3$–C$_7$ cycloalkyl substituted by 1 to 4 groups independently selected from R$^{18}$, C$_3$–C$_6$ cycloalkenyl, t-butoxycarbonyl or

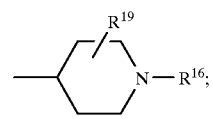

R$^3$ and R$^4$ are independently selected from the group consisting of H, halo, —CF$_3$, C$_1$–C$_6$ alkyl, C$_1$–C$_6$ alkoxy and —OH;

R$^5$ and R$^6$ are independently selected from the group consisting of H, C$_1$–C$_6$ alkyl, —CF$_3$, C$_1$–C$_6$ alkoxy, —OH, C$_1$–C$_6$ alkylcarbonyl, C$_1$–C$_6$ alkoxycarbonyl, R$^{13}$CONH—, (R$^{13}$)$_2$NCO—, R$^{13}$OCONH—, R$^{13}$NHCONH— and NH$_2$CONR$^{13}$—;

R$^7$ is independently selected from the group consisting of C$_1$–C$_6$ alkyl; or the two R$^7$ groups may be joined to form —(C(R$^{14}$)$_2$)$_p$— wherein p is an integer from 2 to 4;

R$^8$, R$^9$, R$^{10}$, R$^{11}$ and R$^{12}$ are independently selected from the group consisting of H, halo, C$_1$–C$_6$ alkyl, C$_1$–C$_6$ alkoxy, benzyloxy, benzyloxy substituted by —NO$_2$ or —N(R$^{14}$), halo C$_1$–C$_6$ alkyl, polyhalo C$_1$–C$_6$ alkyl, —NO$_2$, —CN, —SO$_2$, —OH, —NH$_2$, —N(R$^{14}$)$_2$, —CHO, polyhalo C$_1$–C$_6$ alkoxy, acyloxy, (C$_1$–C$_4$ alkyl)$_3$Si—, (C$_1$–C$_6$ alkyl)SO$_{0-2}$, arylsulfonyl, heteroaryl-sulfonyl, acyl, (C$_1$–C$_6$ alkoxy)CO—, —OCON(R$^{14}$)$_2$, —NHCOO—(C$_1$–C$_6$)alkyl, —NHCO—(C$_1$–C$_6$ alkyl), phenyl, hydroxy(C$_1$–C$_6$ alkyl) or morpholino;

R$^{13}$ is independently selected from the group consisting of H, C$_1$–C$_6$ alkyl, C$_3$–C$_6$ cycloalkyl, —(C$_1$–C$_6$ alkyl)COOR$^{15}$, aryl, heteroaryl, -(C$_1$–C$_6$ alkyl)aryl, -(C$_1$–C$_6$ alkyl)heteroaryl and adamantyl;

R$^{14}$ is independently selected from the group consisting of H and C$_1$–C$_6$ alkyl;

R$^{15}$ is independently selected from the group consisting of H, C$_1$–C$_{20}$ alkyl, C$_3$–C$_6$ cycloalkyl, aryl substituted by 1 to 3 groups independently selected from R$^3$ and heteroaryl substituted by 1 to 3 groups independently selected from R$^3$;

$R^{16}$ is H, $C_1$–$C_6$ alkyl, —$COR^{20}$, $C_1$–$C_6$ alkoxycarbonyl, —$CON(R^{14})_2$, —$CONH(R^3$-aryl), —$SO_{1\text{-}2}$—$R^{15}$, —$SO_{1\text{-}2}$—$(CH_2)_m$—$R^{21}$, —$SON(R^{14})_2$, —$COSR^{14}$ or

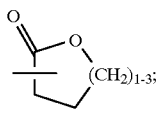

$R^{17}$ is H, $C_1$–$C_6$ alkyl, aryl or heteroaryl;

$R^{18}$ is independently selected from the group consisting of halo, —$CF_3$, $C_1$–$C_6$ alkyl, $C_1$–$C_6$ alkoxy, —OH, =O, —$CON(R^{14})_2$ and —$N(R^{14})COR^{15}$;

$R^{19}$ is H, —OH, $C_1$–$C_{20}$ alkyl, $C_3$–$C_6$ cycloalkyl, aryl substituted by 1 to 3 groups independently selected from $R^3$ or heteroaryl substituted by 1 to 3 groups independently selected from $R^3$;

$R^{20}$ is H, $C_1$–$C_{20}$ alkyl, $C_1$–$C_6$ alkoxy($C_1$–$C_6$)alkyl, $C_3$–$C_6$ cycloalkyl, aryl, aryl($C_1$–$C_6$ alkyl)-, aryloxy, aryloxy($C_1$–$C_6$ alkyl)-, tetrahydrofuranyl or heteroaryl, wherein the aryl or heteroaryl group is substituted by 1 to 3 groups independently selected from $R^3$;

m is 0 to 3; and $R^{21}$ is $C_7$–$C_{10}$ bridged cycloalkyl or $C_7$–$C_{10}$ bridged cycloalkyl wherein the cycloalkyl portion is substituted by 1 or 2 substituents selected from the group consisting of $C_1$–$C_6$ alkyl or =O.

Preferred compounds of formula I are those wherein X is —S—, —SO—, —$SO_2$— or —$CH_2$—, with —$SO_2$— and —$CH_2$— being more preferred. Also preferred are compounds of formula I wherein R is $R^8$, $R^9$, $R^{10}$, $R^{11}$, $R^{12}$-substituted phenyl, preferably alkoxyphenyl, or 3,4-methylenedioxyphenyl, with 3,4-methylenedioxyphenyl being more preferred. $R^3$ and $R^4$ are preferably each hydrogen. $R^2$ is preferably cycloalkyl or

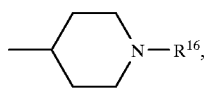

wherein $R^{16}$ is preferably —$COR^{20}$, $C_1$–$C_6$ alkoxycarbonyl or —$SO_2R^{21}$, especially —$COR^{20}$ wherein $R^{20}$ is $R^3$-substituted aryl. When $R^{20}$ is $R^3$-substituted aryl, it is preferably $R^3$-substituted phenyl, especially 2-substituted phenyl wherein the substituent is methyl or halo. $R^5$ and $R^6$ are preferably independently hydrogen and —$CH_3$.

Another aspect of the invention is a pharmaceutical composition comprising a compound having structural formula I in combination with a pharmaceutically acceptable carrier.

Another aspect of the invention is the use of a compound of formula I for the preparation of a pharmaceutical composition useful in the treatment of cognitive disorders and neurodegenerative diseases such as Alzheimer's disease.

Another aspect of this invention is a method for treating a cognitive or neurodegenerative disease comprising administering to a patient suffering from said disease an effective amount of a compound of formula I.

Another aspect of this invention is a method for treating cognitive and neurodegenerative diseases, such as Alzheimer's disease with a compound of formula I in combination with an acetylcholinesterase inhibitor.

Another aspect of this invention is a method for treating a cognitive or neurodegenerative disease comprising administering to a patient suffering from said disease an effective amount of a combination of a compound of formula I as defined above, including stereoisomers, pharmaceutically acceptable salts, esters and solvates thereof, said compound being capable of enhancing acetylcholine (ACh) release (preferably an m2 or m4 selective muscarinic antagonist) with an acetycholinesterase (ACh'ase) inhibitor.

Another aspect of this invention is a kit comprising in separate containers in a single package pharmaceutical compounds for use in combination to treat cognitive disorders in one container a compound of formula I capable of enhancing acetylcholine release (preferably an m2 or m4 selective muscarinic antagonist) in a pharmaceutically acceptable carrier and in a second container an cetylcholinesterase inhibitor in a pharmaceutically acceptable carrier, the ombined quantities being an effective amount.

DETAILED DESCRIPTION

Except where stated otherwise, the following definitions apply throughout the specification and claims. These definitions apply whether a term is used by itself or in combination with other terms.

Alkenyl represents a straight or branched hydrocarbon chain of 2 to 6 carbon atoms having at least one carbon-to-carbon double bond.

Cycloalkyl represents a saturated carbocyclic ring having 3 to 6 carbon atoms. Bridged cycloalkyl represents a $C_7$–$C_{11}$ saturated carbocyclic ring comprised of a $C_3$–$C_6$ cycloalkyl ring and a $C_1$–$C_6$ alkylene chain joined at each end to non-adjacent carbon atoms of the ring; when substituted, the cycloalkyl ring can have 1 to 2 substitutents selected from the group conisisting of $C_1$–$C_6$ alkyl and =O. Examples of optionally substituted bridged cycloalkyl groups are 7,7-dimethyl-5-oxo-bicyclo[2.2.1]hept-4(R)-yl (which, when the group $R^{16}$ is —$SO_2$—$(CH_2)_m$—$R^{21}$ and m is 1, forms a camphorsulfonyl group), adamantyl, mrytanyl, noradamantyl, norbornyl, bicyclo[2.2.1]heptyl, 6,6-dimethylbicyclo[3.1.1]-heptyl, bicyclo[3.2.1]octyl and biclcylo[2.2.2]octyl.

Cycloalkenyl represents a carbocyclic ring having from 3 to 6 carbon atoms and at least one carbon-to-carbon double bond in the ring.

Halo represents fluoro, chloro, bromo or iodo.

Aryl represents optionally substituted phenyl or optionally substituted naphthyl, wherein the substituents are 1 to 3 groups as defined in $R^8$.

Heteroaryl represents optionally substituted heteroaryl groups, wherein the substituents are 1 to 3 groups as defined in $R^8$, and the heteroaryl group is pyridinyl, pyrimidinyl, pyrazinyl, pyridazinyl, thiophenyl, furanyl or pyrolyl.

Polyhalo represent substitution of at least 2 halo atoms to the group modified by the term "polyhalo".

Sulfonyl represents a group of the formula —$SO_2$—.

Sulfinyl represents a group of the formula —SO—.

When a variable appears more than once in the structural formula, for example $R^7$ when X is —$C(OR^7)_2$—, the identity of each variable appearing more than once may be independently selected from the definition for that variable.

Variables $R^5$ and $R^6$ can be attached independently to substitutable carbon atoms in the piperidinyl ring, or both variables can be attached to the same ring carbon atom. Similarly, when $R^2$ is $R^{18}$-substituted cycloalkyl and $R^{18}$ is alkyl, two substituents or one =O group may be attached to any of the methylene ring members.

In the definition of $R^{20}$, any of the substituents having an aryl or heteroaryl portion can be substituted by 1 to 3 $R^3$ groups on substitutable ring carbon atoms of said aryl or heteroaryl groups.

Compounds of this invention may exist in at least two stereo configurations on the carbon to which $R^5$ and/or $R^6$ are attached, except when $R^5$ and $R^6$ are attached to the same carbon and are identical. Further stereoisomerism is present when X is SO, or $C(OR^7)_2$ (when the two $R^7$ groups are not the same). Also within formula I there are numerous other possibilities for stereoisomerism. All possible stereoisomers of formula I are within the scope of the invention.

Compound of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I are prepared by processes known to those skilled in the art as exemplified by the following reaction procedures:

METHOD A

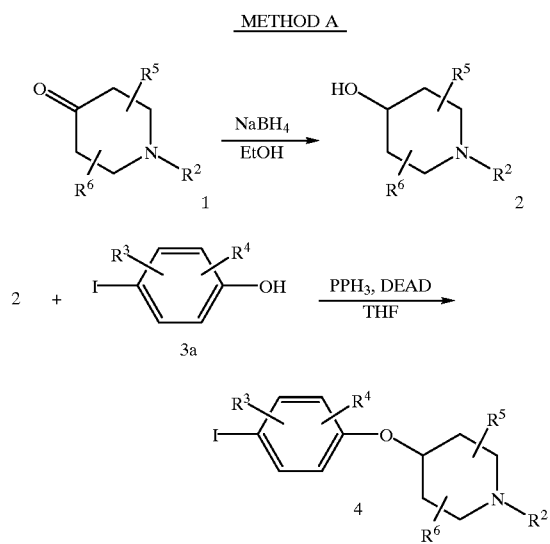

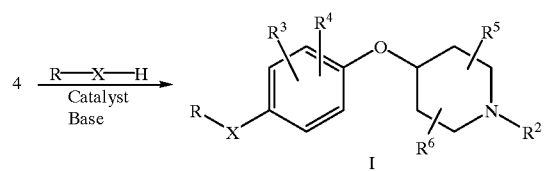

A substituted 4-piperidinone 1 is reduced with $NaBH_4$ and the resulting 4-piperidinol 2 is reacted with a 4-iodophenol derivative, 3a, in the presence of an activator such as diethyl azodicarboxylate (DEAD) and a phosphine such as triphenylphosphine ($PPh_3$), to give a phenyl ether 4. The phenyl ether is reacted with a compound R—X—H, wherein R and X are as defined above, in the presence of a catalyst such as copper iodide to give a compound of formula I.

Alternatively, the following procedure can be used:

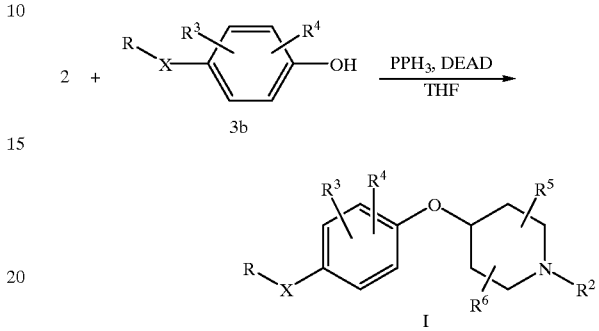

A compound of formula 2 is reacted with a phenol, 3b, in the presence of an activator such as DEAD and a phosphine $PPh_3$ to give a compound of formula I. This alternate route is preferred when X is not S, O, or N.

METHOD B

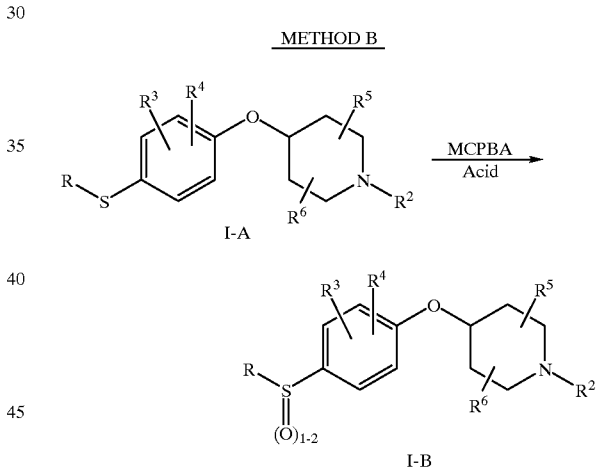

Compounds of formula I-A, wherein X is S, can be converted to compounds of formula I-B, wherein X is $S(O)_{1-2}$, by treatment with an oxidant such as m-chloroperbenzoic acid (MCPBA) in the presence of an organic acid such as methanesulfonic acid.

METHOD C

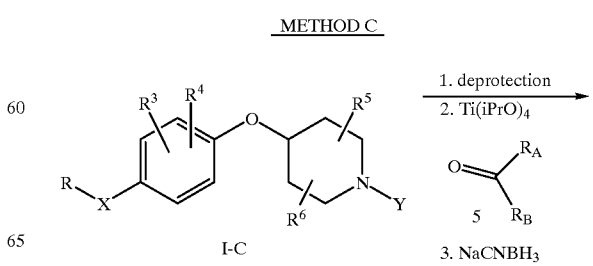

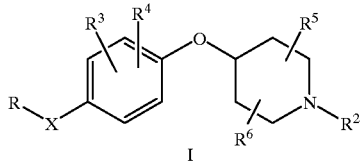

I

Compounds of formula I-C (prepared by Method A and/or B), wherein Y is a suitable nitrogen protecting group, can be transformed into compounds of formula I by removal of the protecting group under standard conditions, followed by reacting the resulting piperidine with a ketone 5, where $R_A$ and $R_B$ together with the attached carbon form $R_2$. The reaction is preferably carried out in the presence of a Lewis acid such as titanium tetraisopropoxide. The resulting iminium ion is treated with a reducing agent such as $NaCNBH_3$ to give a compound of formula I.

METHOD D

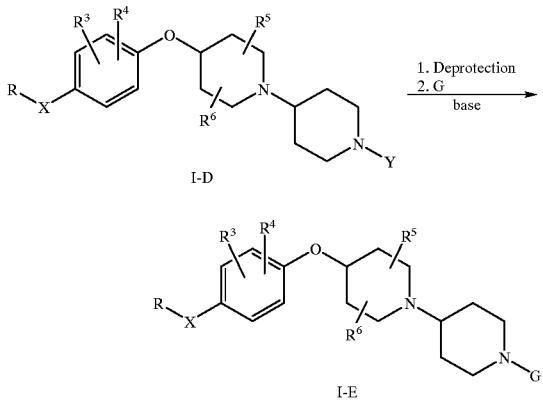

Compounds of the formula I-D, wherein Y is a protecting group, are prepared according to methods A, B, and/or C. Compounds of formula I-D are converted to compounds of formula I-E by deprotection under standard conditions, followed by treatment with a reagent G, wherein G is $R^{16a}L$, wherein $R^{16a}$ is as defined above for $R^{16}$, except it is not H, and L is a leaving group such as Cl or Br; or G is $R^{15a}NCO$, wherein $R^{15a}$ is as defined above for $R^{15}$, except it is not H.

METHOD E

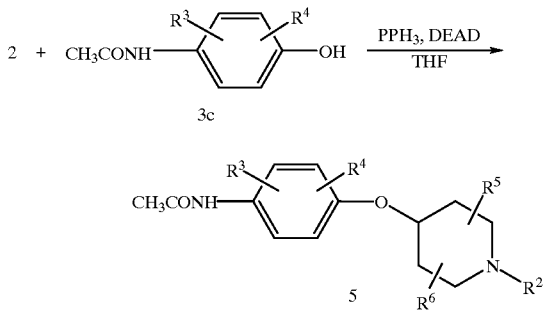

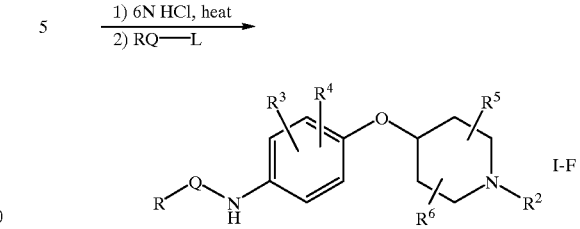

I-F

Compounds of formula I-F, wherein Q is —CO— or —$SO_2$—, are prepared by first preparing a compound of formula 5 using the procedures described in steps 1 and 2 of method A. The compound of formula 5 is then hydrolyzed to an aniline with strong acid such as 6N HCl. The aniline derivative is acylated or sulfonated with an activated reagent $(RCO)_2O$ or RQ-L, where R is as previously defined, Q is as defined above, and L is a leaving group such as halogen or imidazolyl. Examples of activated reagents include RCO-halogen, $RCOOCOCH_3$, ROCO-halogen and $RSO_2$-halogen.

As indicated, in the above processes it is sometimes desirable and/or necessary to protect certain groups during the reactions. Conventional protecting groups, familiar to those skilled in the art, are operable.

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

The compounds of formula I exhibit selective m2 and/or m4 muscarinic antagonizing activity, which has been correlated with pharmaceutical activity for treating cognitive disorders such as Alzheimers disease and senile dementia.

The compounds of formula I display pharmacological activity in test procedures designated to indicate m1, m2 and m4 muscarinic antagonist activity. The compounds are non-toxic at pharmaceutically therapeutic doses.

For preparing pharmaceutical compositions from the compounds of formula I capable of enhancing ACh release, and ACh'ase inhibitors, pharmaceutically acceptable inert carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as dilutents, flavoring agents, solubilizers, lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

When a compound of formula I capable of enhancing ACh release is used in combination with an ACh'ase inhibitor to treat cognitive disorders, these two active components may be co-administered simultaneously or sequentially, or a single pharmaceutical composition comprising a compound of formula I capable of enhancing ACh release and an ACh'ase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the ACh'ase inhibitor may range from 0.001 to 100 mg/kg body weight.

The invention disclosed herein is exemplified by the following preparations and examples which should not be construed to limit the scope of the disclosure. Alternative mechanistic pathways and analogous structures may be apparent to those skilled in the art.

EXAMPLE 1

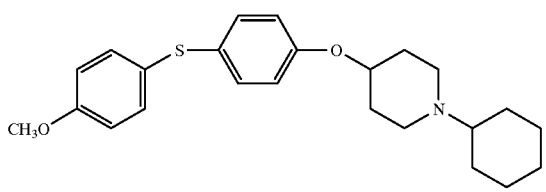

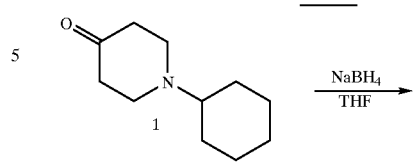

Add NaBH$_4$ (1.2 g) portion-wise to an ice-cold solution of N-cyclo-hexylpiperidine-4-one (1) (10.5 g) in ethanol (EtOH) (200 mL). After the addition is complete, remove the cooling bath and stir the mixture for 24 h at room temperature. Remove the solvent and partition the residue between water and ethyl acetate (EtOAc) (125 mL each). Dry the organic layer over MgSO$_4$ and evaporate to give 9.0 g of the crude product 2 which is used directly in the next step.

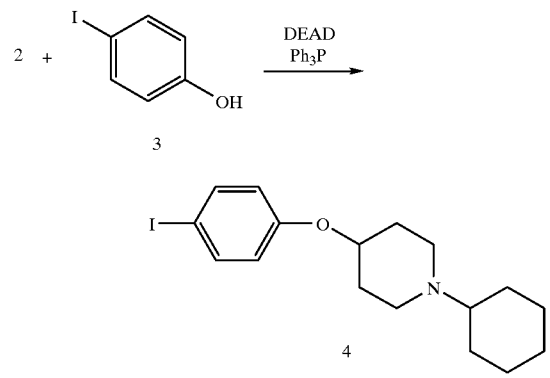

To a solution of 2 in THF (150 mL), add 4-iodophenol (3) (11.08 g) followed by PPh$_3$ (13.1 g). Chill the mixture in an ice bath and slowly, with stirring, add a solution of diethylazodicarboxylate (8.75 g) in THF (10 mL). Stir the resulting mixture overnight while allowing to warm to room temperature. Evaporate the mixture to dryness and take the residue up in EtOAc (250 mL). Wash the EtOAc with 1N HCl (150 mL), dry over MgSO$_4$ and evaporate. Chromatograph the residue on 450 g flash-grade silica gel, eluting with EtOAc followed by CH$_2$Cl$_2$:EtOH:aqueous NH$_3$ (100:3:1) to give 1.5 g of product 4.

Step 3: Heat a solution of 4 (0.58 g), 4-methoxybenzenethiol (0.42 g), CuI (47.6 mg), and K$_2$CO$_3$ (1.0 g) in DMPU (9 mL) under N$_2$ in an oil bath at 140–145° C. for 4.5 h. After cooling to room temperature, pour the mixture into ice water (700 mL) and filter. Dissolve the wet solid in EtOAc (70 mL), dry over MgSO$_4$ and evaporate. Purify the resulting material over 25 g of flash grade silica gel, eluting with EtOAc to give 0.45 grams of oily product. Convert to its hydrochloride to give a solid, mp=223–224° C.

In a similar manner, using appropriate starting materials, the following compounds are prepared:

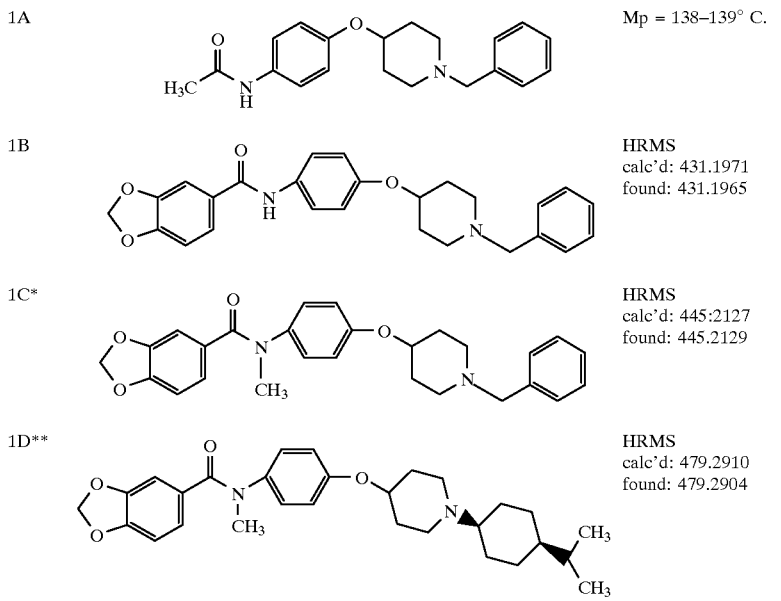

*1C was prepared by adding NaH (0.005 g) to a solution of 1B (0.05 g) at ambient temperature and stirring for 20 min. CH₃I (0.017 g) was added and the reaction mixture was stirred for 2 h. The reaction mixture was diluted with water and extracted with EtOAc. The EtOAc layer was separated and concentrated, and the crude material was purified by silica gel prep. TLC, eluting with acetone/CH₂Cl₂ (¼) to obtain 1C (0.027 g).
**1D is prepared from 1C by debenzylation, followed by reductive amination with the cyclohexanone derivative.

EXAMPLE 2

Treat the product of Example 1 (200 mg) in acetic acid (6 mL) with NaBO₃.4 H₂O (155 mg) and stir the resulting mixture overnight at room temperature. Dilute the mixture with water and basify with K₂CO₃. Extract the solution with CH₂Cl₂ (2×30 mL). Dry the combined organic layers over MgSO₄ and evaporate to give 200 mg of an oily residue which is predominantly sulfoxone A, with a lesser amount of sulfoxide B. (Using 82 mg of NaBO₃.4 H₂O results in the sulfoxide B predominating.) Separate the sulfoxide and sulfone by chromatography over flash grade silica gel, eluting with CH₂Cl₂:EtOH:aqueous NH₃ (100:3:1) to give:
  A: mp=250–252° C. (HCl salt); and
  B: gummy solid.

EXAMPLE 3

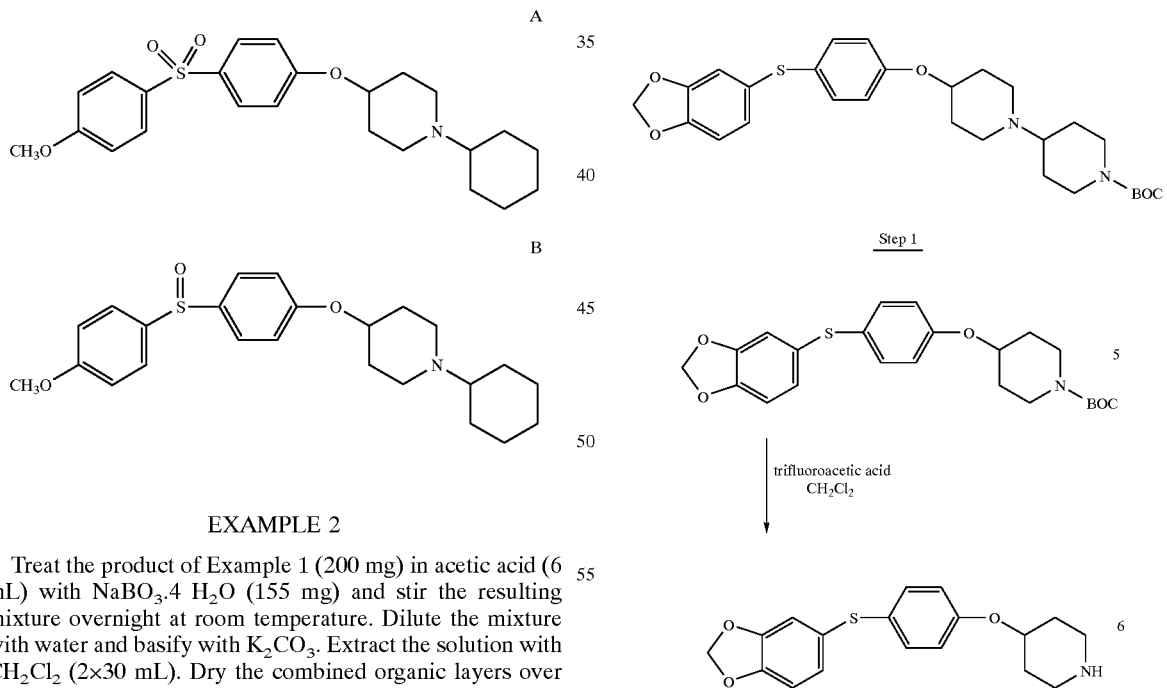

Treat a solution of compound 5, prepared via method A, in CH₂Cl₂ (15 mL) with trifluoroacetic acid (3 mL) and stir the resulting mixture 30 min. at room temperature. After evaporating to dryness, add the residue to 1N NaOH and extract with CH₂Cl₂. After drying over Na₂SO₄, evaporate the solvent to give 1.0 grams of compound 6.

Step 2: To a mixture of the product of Step 1 and N—BOC-4-piperidinone in CH₂Cl₂ (10 mL), add titanium tetraisopropoxide (3.4 mL) and stir the mixture overnight at room temperature. To this mixture, add NaCNBH₃ (0.74 g) in CH₃OH (4 mL) and stir the reaction under N₂ for 5 h. Quench the reaction by adding a mixture of 1N NaOH (50 mL) and EtOAc (100 mL) and stir for 1 h. Filter the reaction and extract the filtrate with EtOAc. After drying over NaHCO₃, remove the solvent and purify the residue by chromatography to give 1.32 g of the title compound.
HRMS: calc'd: 500.2471; found: 500.2465.

In a similar manner, using appropriate starting materials, the following compound is prepared:

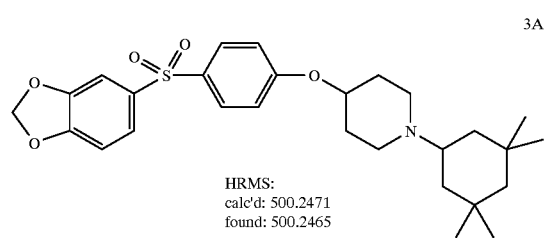

HRMS:
calc'd: 500.2471
found: 500.2465

EXAMPLE 4

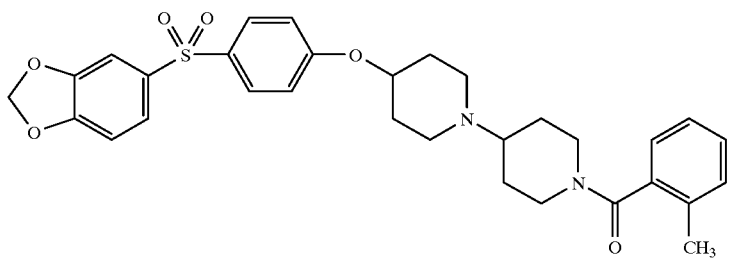

Step 1: Dissolve the product of Example 3 (0.55 g) in CH₂Cl₂ (8 mL) and add CH₃SO₃H (0.2 mL). After stirring for 20 min., add MCPBA (0.93 g of 50–60%) and stir the reaction for 4 h at room temperature. Add the reaction mixture to 1N NaOH (50 mL), stir for 30 min. and extract with CH₂Cl₂. Dry the organic layer over NaHCO₃ and evaporate to obtain 0.45 grams of the desired 1,4-bipiperidine derivative.

Step 2: To the product of Step 1 (65 mg) in CH₂Cl₂ (2 mL), add triethylamine (Et₃N) (0.5 mL) followed by o-toluoyl chloride (35 mg). Stir the reaction mixture at room temperature for 1.5 h under N₂, then apply directly to a preparative silica gel TLC plate, eluting with 5% CH₃OH in CH₂Cl₂ to obtain 60 mg of the title compound.
HRMS: calc'd: 563.2216; found: 563.2211.

In a similar manner, using appropriate starting materials, compounds of the following structural formula are prepared, wherein the variables are as defined in the table:

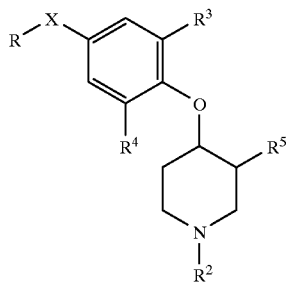

| Ex. | R | X | R² | R³' | R⁵ | HRMS |
|---|---|---|---|---|---|---|
| 4A | H₃CO—⟨phenyl⟩— | —SO₂— | ⟨piperidinyl-N=S(=O)-CH₂CH₃⟩ | H, H | H | calc'd: 537.2093 found: 537.2091 |

-continued
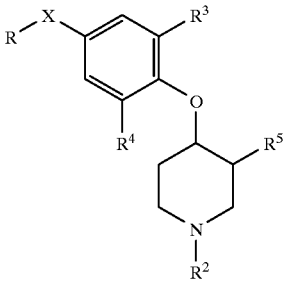
| Ex. | R | X | R² | R³' | R⁵ | HRMS |
|---|---|---|---|---|---|---|
| 4B | 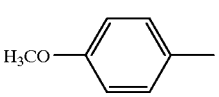 | —SO₂— | 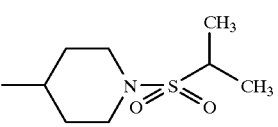 | H, H | H | calc'd: 537.2093 found: 537.2097 |
| 4C | 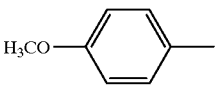 | —SO₂— | 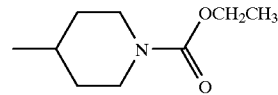 | H, H | H | calc'd: 503.2216 found: 503.2214 |
| 4D | 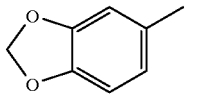 | —SO₂— | 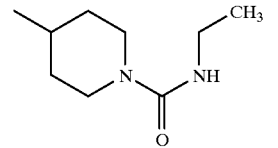 | H, H | H | calc'd: 516.2168 found: 516.2171 |
| 4E | 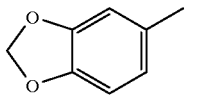 | —SO₂— | 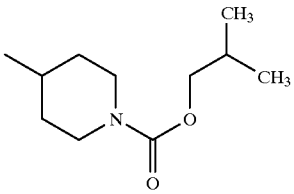 | H, H | H | calc'd: 545.2321 found: 545.2325 |
| 4F | 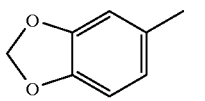 | —SO₂— | 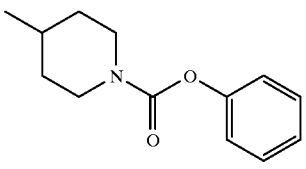 | H, H | H | calc'd: 565.2008 found: 565.2007 |
| 4G | 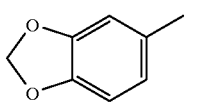 | —SO₂— | 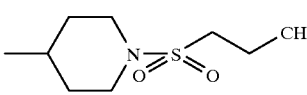 | H, H | H | calc'd: 551.1886 found: 551.1886 |
| 4H | 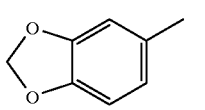 | —SO₂— | 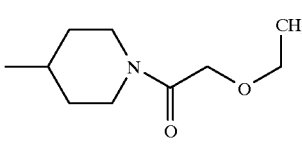 | H, H | H | calc'd: 531.2165 found: 531.2172 |
| 4I | 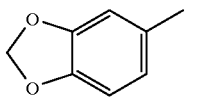 | —SO₂— | 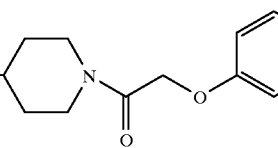 | H, H | H | calc'd: 579.2165 found: 579.2157 |

-continued

| Ex. | R | X | R² | R³' | R⁵ | HRMS |
|---|---|---|---|---|---|---|
| 4J | benzodioxole | —SO₂— | 4-methylpiperidine-N-C(O)OCH₂CH₃ | H, H | H | calc'd: 517.2008 found: 517.2004 |
| 4K | benzodioxole | —SO₂— | 4-methylpiperidine-N-C(O)-(2-methoxyphenyl) | H, H | H | calc'd: 579.2165 found: 579.2160 |
| 4L | benzodioxole | —SO₂— | 4-methylpiperidine-N-SO₂CH₂CH₃ | H, H | H | calc'd: 537.1729 found: 537.1730 |
| 4M | benzodioxole | —SO₂— | 4-methylpiperidine-N-SO₂-(3,4-dimethoxyphenyl) | H, H | H | calc'd: 645.1940 found: 645.1933 |
| 4N | benzodioxole | —SO₂— | 4-methylpiperidine-N-SO₂CH(CH₃)₂ | H, H | H | calc'd: 551.1886 found: 551.1885 |
| 4O | benzodioxole | —SO₂— | 4-methylpiperidine-N-SO₂(CH₂)₃CH₃ | H, H | H | calc'd: 565.2042 found: 565.2029 |
| 4P | benzodioxole | —SO₂— | 4-methylpiperidine-N-(tetrahydrofuran-2-one-3-yl) | H, H | H | calc'd: 529.2008 found: 529.2007 |
| 4Q | benzodioxole | —SO₂— | 4-methylpiperidine-N-C(O)-(tetrahydrofuran-2-yl) | H, H | H | calc'd: 543.2165 found: 543.2165 |

-continued

| Ex. | R | X | R² | R³' | R⁵ | HRMS |
|---|---|---|---|---|---|---|
| 4R | benzo[1,3]dioxol-5-yl | —SO₂— | 4-methylpiperidine-1-carbothioic acid S-methyl ester | H, H | H | calc'd: 519.1624 found: 519.1634 |
| 4S | benzo[1,3]dioxol-5-yl | —SO₂— | 4-methylpiperidine-1-carboxylic acid dimethylamide | H, H | H | calc'd: 516.2168 found: 516.2171 |
| 4T | benzo[1,3]dioxol-5-yl | —SO₂— | 1-(benzylsulfonyl)-4-methylpiperidine | H, H | H | calc'd: 599.1886 found: 599.1883 |
| 4U | benzo[1,3]dioxol-5-yl | —SO₂— | 4-methylpiperidine-1-sulfonic acid dimethylamide | H, H | H | calc'd: 552.1838 found: 552.1831 |
| 4V | benzo[1,3]dioxol-5-yl | —SO₂— | camphorsulfonyl-4-methylpiperidine | H, H | H | calc'd: 659.2561 found: 659.2557 |
| 4W | benzo[1,3]dioxol-5-yl | —SO₂— | camphorsulfonyl-4-methylpiperidine (enantiomer) | H, H | H | calc'd: 659.2461 found: 659.2444 |
| 4X | benzo[1,3]dioxol-5-yl | —SO₂— | 1-(2,5-dimethoxyphenylsulfonyl)-4-methylpiperidine | H, H | H | calc'd: 645.1940 found: 645.1954 |

-continued

| Ex. | R | X | R² | R³' | R⁵ | HRMS |
|---|---|---|---|---|---|---|
| 4Y | 1,3-benzodioxol-5-yl | —SO₂— | 4-methylpiperidine-1-sulfonyl(2-methylphenyl) | H, H | H | calc'd: 599.1886 found: 599.1886 |
| 4Z | 1,3-benzodioxol-5-yl | —SO₂— | 4-methyl-1-benzoylpiperidine | H, H | H | calc'd: 549.2059 found: 549.2071 |
| 4AA | 1,3-benzodioxol-5-yl | —SO₂— | 4-methylpiperidine-1-sulfonyl propyl | —CH₃, H | H | calc'd: 565.2042 found: 565.2045 |
| 4AB | 1,3-benzodioxol-5-yl | —SO₂— | 4-methylpiperidine-1-carboxylic acid phenyl ester | —CH₃, H | H | calc'd: 579.2165 found: 579.2181 |
| 4AC | 1,3-benzodioxol-5-yl | —SO₂— | 4-methylpiperidine-1-sulfonyl ethyl | —CH₃, H | H | calc'd: 551.1886 found: 551.1890 |
| 4AD | 1,3-benzodioxol-5-yl | —SO₂— | 4-methyl-1-(2-methylbenzoyl)piperidine | —CH₃, H | H | calc'd: 577.2372 found: 577.2370 |
| 4AE | 1,3-benzodioxol-5-yl | —SO₂— | 4-methyl-1-benzoylpiperidine | —CH₃, H | H | calc'd: 563.2216 found: 563.2228 |

-continued

| Ex. | R | X | R² | R³', R⁴ | R⁵ | HRMS |
|---|---|---|---|---|---|---|
| 4AF | benzo[1,3]dioxol-5-yl | —SO₂— | 4-methylpiperidine-1-carboxylic acid tert-butyl ester | —CH₃, H | H | calc'd: 559.2478<br>found: 559.2472 |
| 4AG (1) | benzo[1,3]dioxol-5-yl | —SO₂— | 4-methyl-1-(2-chlorobenzoyl)piperidine | H, H | —CH₃ | calc'd: 597.1826<br>found: 597.1840<br>(isomer E) |
| 4AG (2) | benzo[1,3]dioxol-5-yl | —SO₂— | 4-methyl-1-(2-chlorobenzoyl)piperidine | H, H | —CH₃ | calc'd: 597.1826<br>found: 597.1840<br>(isomer A) |
| 4AH | benzo[1,3]dioxol-5-yl | —SO₂— | 4-methyl-1-(2-chlorobenzoyl)piperidine | H, H | H | calc'd: 583.1670<br>found: 583.1666 |
| 4AI | benzo[1,3]dioxol-5-yl | —SO₂— | 4-methyl-1-(2-bromobenzoyl)piperidine | H, H | H | calc'd: 627.1164<br>found: 627.1167 |
| 4AJ | benzo[1,3]dioxol-5-yl | —CH₂— | 4-methyl-1-(2-methylbenzoyl)piperidine | H, H | H | calc'd: 513.2573<br>found: 513.2760 |
| 4AK | benzo[1,3]dioxol-5-yl | —CH₂— | 4-methyl-1-(2-chlorobenzoyl)piperidine | H, H | H | calc'd: 533.2207<br>found: 533.2217 |

-continued

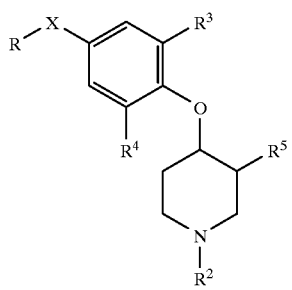

| Ex. | R | X | R² | R³', | R⁵ | HRMS |
|---|---|---|---|---|---|---|
| 4AL | benzo[1,3]dioxol-5-yl | —SO₂— | 4-methyl-1-[(3-methylthiophen-2-yl)carbonyl]piperidinyl | —CH₃, H | H | calc'd: 583.1937 found: 583.1939 |
| 4AM | benzo[1,3]dioxol-5-yl | —SO₂— | 4-methyl-1-[(3-methylthiophen-2-yl)carbonyl]piperidinyl | H, H | H | calc'd: 569.1780 found: 569.1773 |
| 4AN | benzo[1,3]dioxol-5-yl | —SO₂— | 4-methyl-1-(2-chlorobenzoyl)piperidinyl | —CH₃, H | H | calc'd: 597.1826 found: 597.1846 |
| 4AO | benzo[1,3]dioxol-5-yl | —SO₂— | 4-methyl-1-[(2-methylphenyl)carbamoyl]piperidinyl | H, H | H | calc'd: 578.2325 found: 578.2313 |
| 4AP | benzo[1,3]dioxol-5-yl | —SO₂— | 4-methyl-1-[(2-chlorophenyl)carbamoyl]piperidinyl | H, H | H | calc'd: 598.1779 found: 598.1770 |
| 4AR | benzo[1,3]dioxol-5-yl | —SO₂— | 4-methyl-1-(2,3-dimethylbenzoyl)piperidinyl | H, H | H | calc'd: 577.2372 found: 577.2358 |
| 4AS | benzo[1,3]dioxol-5-yl | —SO₂— | 4-methyl-1-(2,3-dimethylbenzoyl)piperidinyl | —CH₃, H | H | calc'd: 591.2529 found: 591.2523 |

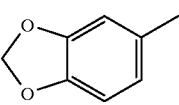
| Ex. | R | X | R² | R³' | R⁵ | HRMS |
|---|---|---|---|---|---|---|
| 4AT | 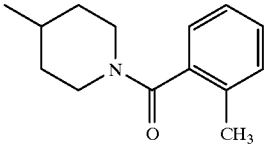 | —SO₂— | 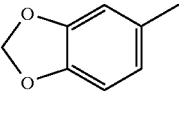 | —CH₃, —CH₃ | H | calc'd: 591.2529 found: 591.2530 |
| 4AU | 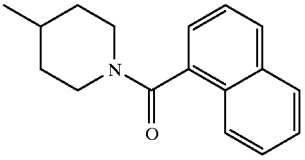 | —SO₂— | 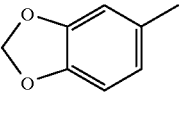 | H, H | H | calc'd: 599.2216 found: 599.2205 |
| 4AV | 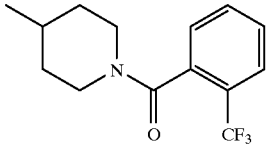 | —SO₂— | 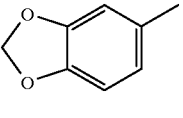 | H, H | H | calc'd (M + 1): 617.1933 found: 617.1920 |
| 4AW | 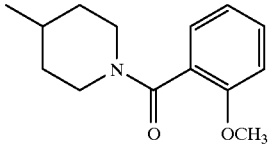 | —SO₂— | 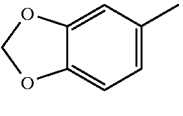 | —CH₃, H | H | calc'd: 593.2321 found: 593.2324 |
| 4AX | 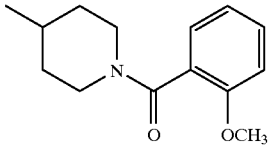 | —CH₂— | 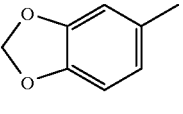 | H, H | H | calc'd (M + 1): 529.2702 found: 529.2702 |
| 4AY | 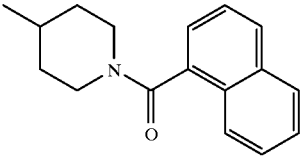 | —SO₂— | 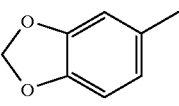 | —CH₃, H | H | calc'd (M + 1): 613.2372 found: 613.2382 |
| 4AZ | 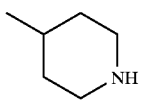 | —SO₂— | | H, H | H | (m.p. = 72–74° C.) |

-continued
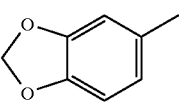
| Ex. | R | X | R² | R³' | R⁵ | HRMS |
|---|---|---|---|---|---|---|
| 4BA | 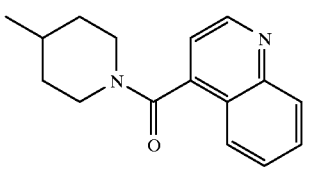 | —SO₂— |  | H, H | H | calc'd (M + 1): 600.2168 found: 600.2162 |
| 4BB | 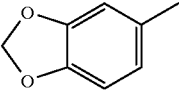 | —SO₂— | 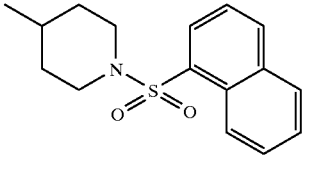 | H, H | H | calc'd (M + 1): 635.1886 found: 635.1889 |
| 4BC |  | —SO₂— | 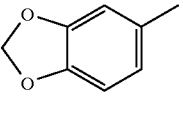 | H, H | H | calc'd (M + 1): 676.1554 found: 676.1569 |
| 4BD | 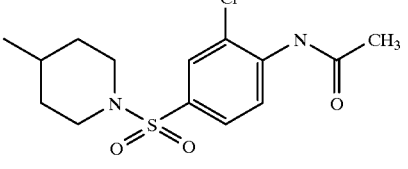 | —SO₂— |  | H, H | H | calc'd (M + 1): 614.2325 found: 614.2340 |
| 4BE | 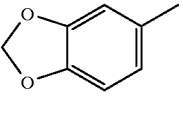 | —SO₂— | 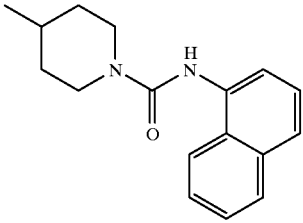 | H, H | H | calc'd (M + 1): 600.2168 found: 600.2162 |
| 4BF |  | —SO₂— | 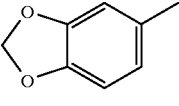 | H, H | H | (LRMS (M − 1): found: 623) |

-continued

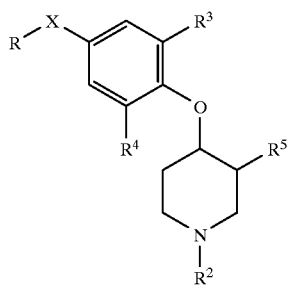

| Ex. | R | X | R² | R³', | R⁵ | HRMS |
|---|---|---|---|---|---|---|
| 4BG | benzo[d][1,3]dioxol-5-yl | —SO— | 4-methyl-1-(biphenyl-2-ylcarbonyl)piperidin-4-yl | H, H | H | (LRMS (M − 3): found: 605) |
| 4BH | benzo[d][1,3]dioxol-5-yl | —SO₂— | 4-methyl-1-(2,3-dichlorobenzoyl)piperidin-4-yl | —CH₃, H | H | calc'd (M + 1): 631.1436 found: 631.1439 |
| 4BI | benzo[d][1,3]dioxol-5-yl | —SO₂— | 4-methyl-1-(3,4-dichlorothiophen-2-ylcarbonyl)piperidin-4-yl | H, H | H | calc'd (M + 1): 6 found: 6 |
| 4BJ | benzo[d][1,3]dioxol-5-yl | —SO₂— | 4-methyl-1-(quinolin-4-ylcarbonyl)piperidin-4-yl | —CH₃, H | H | calc'd (M + 1): 614.2325 found: 614.2334 |
| 4BK | benzo[d][1,3]dioxol-5-yl | —SO₂— | 4-methyl-1-(quinolin-5-ylcarbonyl)piperidin-4-yl | —CH₃, H | H | calc'd (M + 1): 614.2325 found: 614.2328 |

EXAMPLE 5

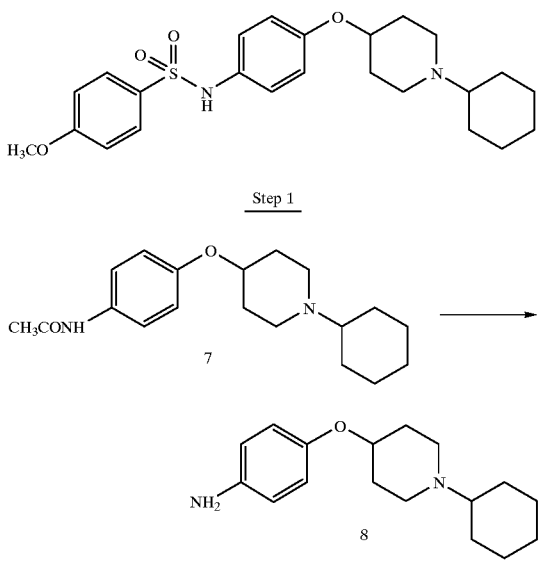

Dissolve compound 7 (0.57 g) (prepared via Method A) in 6N HCl and heat at 100° C. for 5 h. Cool the reaction mixture to ambient temperature and dilute with ice/water. Basify the reaction mixture with 3N NaOH and extract with EtOAc. Separate the organic layer and concentrate to give 0.41 g of product 8.

Step 2: Add 4-methoxybenzenesulfonyl chloride (75 mg) to a solution of 100 mg of product 8 in THF (3 mL) containing Et$_3$N (74 mg) at 0° C. Stir the reaction mixture overnight while warming to ambient temperature. Pour the reaction mixture into half-saturated NaHCO$_3$ solution and extract with EtOAc. Concentate the organic layer and purify on silica gel, eluting with Et$_2$O:Et$_3$N (96:4) to give 50 mg of the title compound. M.p.=112–118° C. (HCl salt).

In a similar manner, using appropriate starting materials, the following compound is prepared:

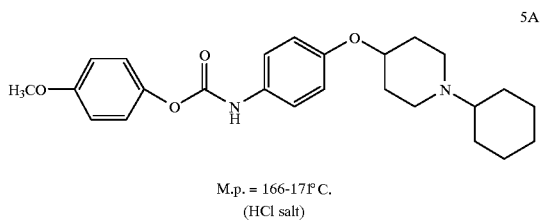

M.p. = 166-17F C.
(HCl salt)

Following are descriptions of the pharmacological test procedures.

MUSCARINIC BINDING ACTIVITY

The compound of interest is tested for its ability to inhibit binding to the cloned human m1, m2, m3 and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homgenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 µg of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 µM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for IC$_{50}$ values (i.e. the concentration of compound required to inhibit binding by 50%) using the EBDA computer program (McPherson, 1985). Affinity values (K$_i$) were then determined using the following formula (Cheng and Prusoff, 1973);

$$K_i = \frac{IC_{50}}{1 + \left[\frac{\text{concentration of radioligand}}{\text{affinity}(K_D) \text{ of radioligand}}\right]}$$

Hence a lower value of K$_i$ indicates greater binding affinity.

The following publications, the entire contents of which are incorporated herein by reference, explain the procedure in more detail.

Cheng, Y. -C. and Prusoff, W. H., Relationship between the inhibitory constant (K$_i$) and the concentration of inhibitor which causes 50 per cent inhibition (IC$_{50}$) of an enzymatic reaction. Biochem. Pharmacol. 22: 3099–3108, 1973.

McPherson, G. A. Kinetic, EBDA, Ligand, Lowry: A Collection of Radioligand Binding Analysis Programs. Elsevier Science Publishers BV, Amsterdam, 1985.

Watson, M. J, Roeske, W. R. and Yamamura, H. I. [$^3$H]Pirenzepine and (-)[$^3$H)quinuclidinyl benzilate binding to rat cerebral cortical and cardiac muscarinic cholinergic sites. Characterization and regulation of antagonist binding to putative muscarinic subtypes. J. Pharmacol. Exp. Ther. 237: 411–418, 1986.

To determine the degree of selectivity of a compound for binding the m2 receptor, the K$_i$ value for m1 receptors was divided by the K$_i$ value for m2 receptors. A higher ratio indicates a greater selectivity for binding the m2 muscarinic receptor. A similar calculation is made to determine the m4 selectivity.

MICRODIALYSIS METHODOLOGY

The following procedure is used to show that a compound functions as an m2 antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12,3 mm×0.5 mm) to a depth of 3 mm in striatum beyond the end of the guide. The probe was connected beforehand with tubing to a microinjection pump (CMA-/100). Rats were collared, tethered, and, following probe insertion, were placed in a large, clear, plexiglass bowl with litter material and access to food and water. The probe was perfused at 2 µl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 µM neostigmine bromide at pH 7.4). To achieve stable baseline readings, microdialysis was allowed to proceed for 90 minutes prior to the collection of fractions. Fractions (20 µl) were obtained at 10 minute intervals over a 3 hour period using a refrigerated collector (CMA/170 or 200). Four to five baseline fractions were collected, following which the drug or combination of drugs to be tested was administered to the animal. Upon completion of the collection, each rat was autopsied to determine accuracy of probe placement.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic m2 receptor antagonism.

In general, compounds in accordance with formula I were tested with the following ranges of results:

$K_i$ binding to m1 receptor, nM: 7.29 to 999.20.

$K_i$ binding to m2 receptor, nM: 0.23 to 167.90.

$K_i$ binding to m3 receptor, nM: 8 to 607.50.

$K_i$ binding to m4 receptor, nM: 1.78 to 353.66.

Compounds of formula I in combination with an ACh' ase inhibitor have an effect on ACh release. The present invention therefore also relates to administering a compound of formula I in combination with any other ACh' ase inhibitor including, but not limited to, E-2020 (available from Eisai Pharmaceutical) and heptylphysostigmine.

What is claimed:

1. A compound having the structural formula

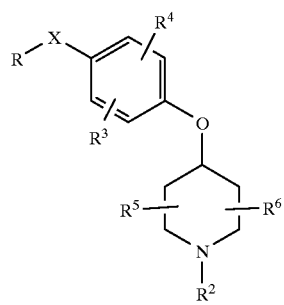

I or an isomer, pharmaceutically acceptable salt, ester or solvate thereof, wherein X is a bond, —O—, —S—, —SO—, —$SO_2$—, —CO—, —C($OR^7$)$_2$—, —$CH_2$—O—, —O—$CH_2$—, —CH═CH—, —$CH_2$—, —CH($C_1$–$C_6$ alkyl)-, —C($C_1$–$C_6$ alkyl)$_2$-, —$CONR^{17}$—, —$NR^{17}CO$—, —O—C(O)$NR^{17}$—, —$NR^{17}$C(O)—O—, —$SO_2NR^{17}$— or —$NR^{17}SO_2$—;

R is $C_3$–$C_6$ cycloalkyl,

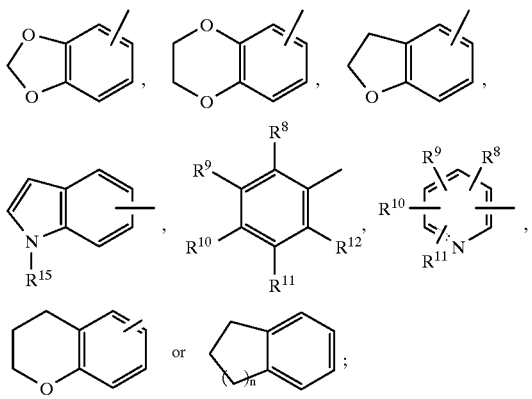

n is 1, 2 or 3;

$R^2$ is $R^3$ and $R^4$ are independently selected from the group consisting of H, halo, —$CF_3$, $C_1$–$C_6$ alkyl, $C_1$–$C_6$ alkoxy and —OH;

$R^5$ and $R^6$ are independently selected from the group consisting of H, $C_1$–$C_6$ alkyl, —$CF_3$, $C_1$–$C_6$ alkoxy, —OH, $C_1$–$C_6$ alkylcarbonyl, $C_1$–$C_6$ alkoxycarbonyl, $R^{13}CONH$—, ($R^{13}$)$_2$NCO—, $R^{13}OCONH$—, $R^{13}NHCONH$— and $NH_2CONR^{13}$—;

$R^7$ is independently selected from the group consisting of $C_1$–$C_6$ alkyl; or the two $R^7$ groups may be joined to form —(C($R^{14}$)$_2$)$_p$— wherein p is an integer from 2 to 4;

$R^8$, $R^9$, $R^{10}$, $R^{11}$ and $R^{12}$ are independently selected from the group consisting of H, halo, $C_1$–$C_6$ alkyl, $C_1$–$C_6$ alkoxy, benzyloxy, benzyloxy substituted by —NO$_2$ or —N(R$^{14}$), halo C$_1$–C$_6$ alkyl, polyhalo C$_1$–C$_6$ alkyl, —NO$_2$, —CN, —SO$_2$, —OH, —NH$_2$, —N(R$^{14}$)$_2$, —CHO, polyhalo C$_1$–C$_6$ alkoxy, acyloxy, (C$_1$–C$_4$ alkyl)$_3$Si—, (C$_1$–C$_6$ alkyl)SO$_{0-2}$, arylsulfonyl, acyl, (C$_1$–C$_6$ alkoxy)CO—, —OCON(R$^{14}$)$_2$, —NHCOO—(C$_1$–C$_6$)alkyl, —NHCO—(C$_1$–C$_6$ alkyl), phenyl, hydroxy(C$_1$–C$_6$ alkyl) or morpholino;

R$^{13}$ is independently selected from the group consisting of H, C$_1$–C$_6$ alkyl, C$_3$–C$_6$ cycloalkyl, —(C$_1$–C$_6$ alkyl)COOR$^{15}$, aryl, —(C$_1$–C$_6$ alkyl)aryl, and adamantyl;

R$^{14}$ is independently selected from the group consisting of H and C$_1$–C$_6$ alkyl;

R$^{15}$ is independently selected from the group consisting of H, C$_1$–C$_{20}$ alkyl, C$_3$–C$_6$ cycloalkyl, and aryl substituted by 1 to 3 groups independently selected from R$^3$;

R$^{16}$ is H, C$_1$–C$_6$ alkyl, —COR$^{20}$, C$_1$–C$_6$ alkoxycarbonyl, —CON(R$^{14}$)$_2$, —CONH(R$^3$-aryl), —SO$_{1-2}$—R$^{15}$, —SO$_{1-2}$—(CH$_2$)$_m$—R$^{21}$, —SON(R$^{14}$)$_2$, —COSR$^{14}$ or

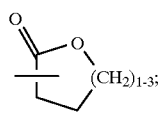

R$^{17}$ is H, C$_1$–C$_6$ alkyl, or aryl;

R$^{18}$ is independently selected from the group consisting of halo, —CF$_3$, C$_1$–C$_6$ alkyl, C$_1$–C$_6$ alkoxy, —OH, =O, —CON(R$^{14}$)$_2$ and —N(R$^{14}$)COR$^{15}$;

R$^{19}$ is H, —OH, C$_1$–C$_{20}$ alkyl, C$_3$–C$_6$ cycloalkyl, or aryl substituted by 1 to 3 groups independently selected from R$^3$;

R$^{20}$ is H, C$_1$–C$_{20}$ alkyl, C$_1$–C$_6$ alkoxy(C$_1$–C$_6$)alkyl, C$_3$–C$_6$ cycloalkyl, aryl, aryl(C$_1$–C$_6$ alkyl)-, aryloxy, aryloxy(C$_1$–C$_6$ alkyl)-, tetrahydrofuranyl or heteroaryl, wherein the aryl or heteroaryl group is substituted by 1 to 3 groups independently selected from R$^3$, wherein heteroaryl is selected from the group consisting of pyridinyl, pyrimidinyl, pyrazinyl, pyridazinyl, thiophenyl, furanyl, pyrolyl or quinolyl;

m is 0 to 3; and

R$^{21}$ is C$_7$–C$_{10}$ bridged cycloalkyl or C$_7$–C$_{10}$ bridged cycloalkyl wherein the cycloalkyl portion is substituted by 1 or 2 substituents selected from the group consisting of C$_1$–C$_6$ alkyl or =O.

2. A compound of claim 1 wherein X is —S—, —SO—, —SO$_2$—or —CH$_2$—.

3. A compound of claim 1 wherein R is

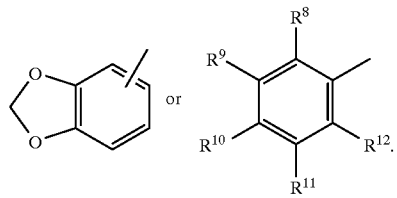

4. A compound of claim 1 wherein R$^3$ and R$^4$ are each hydrogen.

5. A compound of claim 1 wherein R$^2$ is

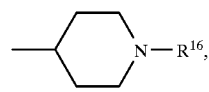

wherein R$^{16}$ is —C(O)—R$^{20}$, C$_1$–C$_6$ alkoxycarbonyl or —SO$_2$R$^{15}$.

6. A compound of claim 5 wherein R$^2$ is

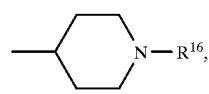

R$^{16}$ is —C(O)—R$^{20}$ and R$^{20}$ is R$^3$-substituted phenyl.

7. A compound of claim 1 wherein R$^5$ and R$^6$ are independently hydrogen or methyl.

8. A compound of claim 1 wherein X is —SO$_2$— or —CH$_2$—; R is 3,4-methylenedioxyphenyl or alkoxyphenyl; R$^3$ and R$^4$ are hydrogen; R$^2$ is

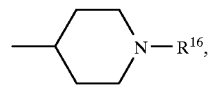

wherein R$^{16}$ is —C(O)—R$^{20}$ and wherein R$^{20}$ is R$^3$-substituted phenyl; and R$^5$ and R$^6$ are independently hydrogen or methyl.

9. A compound as defined in claim 1 selected from the group consisting of compounds represented by the formula

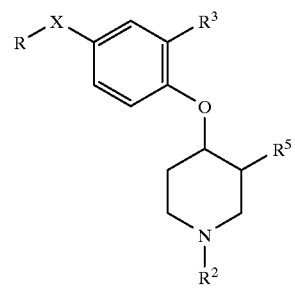

wherein R, X, R$^2$, R$^3$ and R$^5$ are as defined in the following table

| R | X | R² | R³ | R⁵ |
|---|---|---|---|---|
| 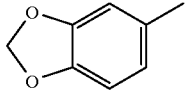 | —SO₂— | 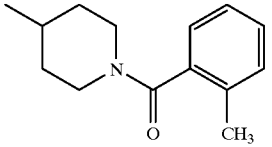 | H | H |
| 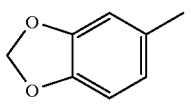 | —SO₂— | 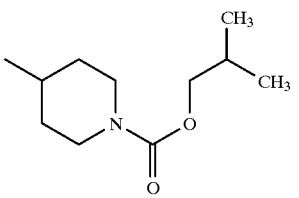 | H | H |
| 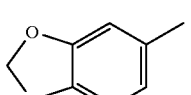 | —SO₂— | 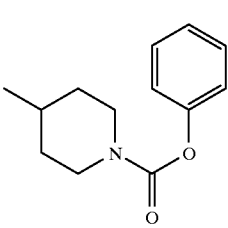 | H | H |
| 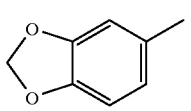 | —SO₂— | 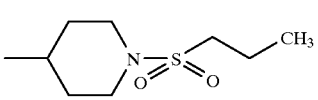 | H | H |
| 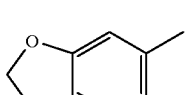 | —SO₂— | 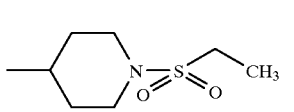 | H | H |
| 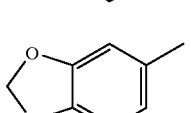 | —SO₂— | 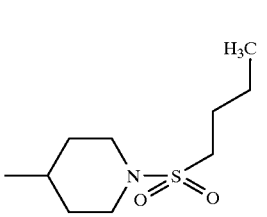 | H | H |
| 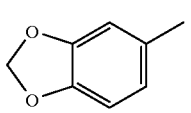 | —SO₂— | 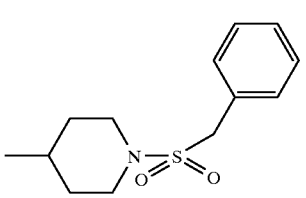 | H | H |
| 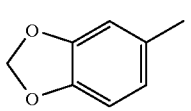 | —SO₂— | 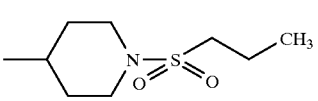 | —CH₃ | H |
| 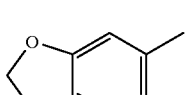 | —SO₂— | 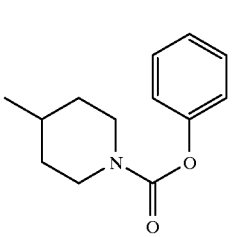 | —CH₃ | H |

-continued
| R | X | R² | R³ | R⁵ |
|---|---|----|----|----|
| 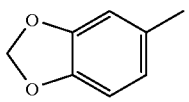 | —SO₂— | 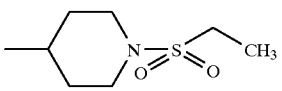 | —CH₃ | H |
| 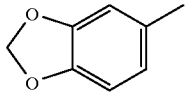 | —SO₂— | 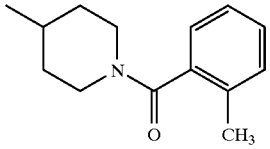 | —CH₃ | H |
| 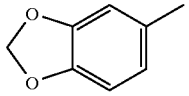 | —SO₂— | 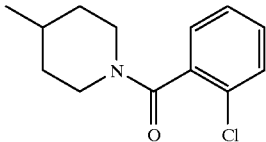 | H | —CH₃ |
| 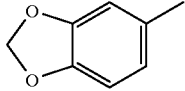 | —SO₂— | 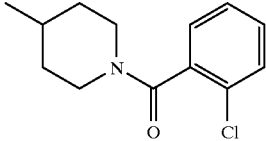 | H | —CH₃ |
| 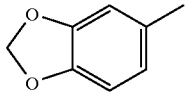 | —SO₂— | 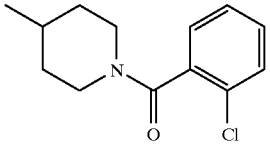 | H | H |
| 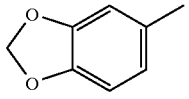 | —SO₂— | 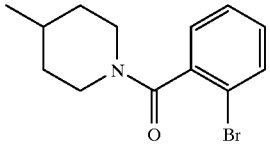 | H | H |
| 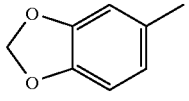 | —CH₂— | 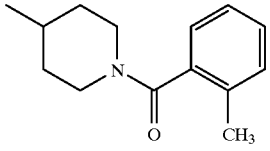 | H | H |
| 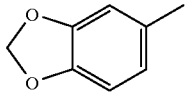 | —SO₂— | 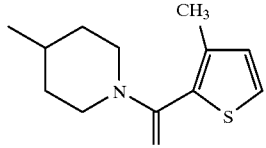 | —CH₃ | H |
| 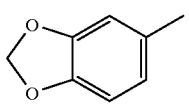 | —SO₂— | 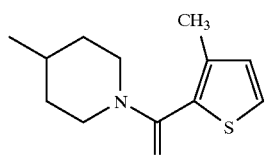 | H | H |

-continued

| R | X | R² | R³ | R⁵ |
|---|---|---|---|---|
| 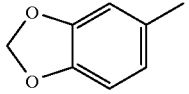 | —SO₂— | 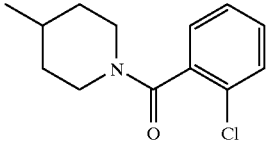 | —CH₃ | H |
| 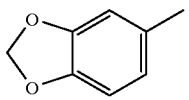 | —SO₂— | 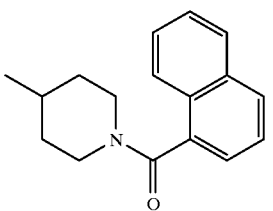 | H | H |
| 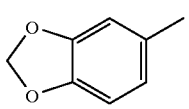 | —SO₂— | 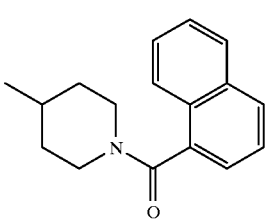 | —CH₃ | H |
| 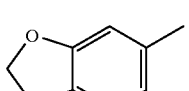 | —SO₂— | 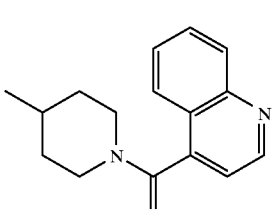 | H | H |
| 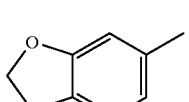 | —SO₂— | 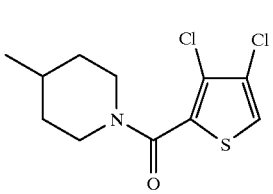 | H | H |
| 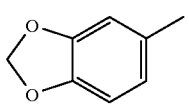 | —SO₂— | 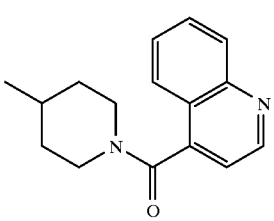 | —CH₃ | H |
| 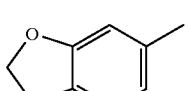 | —SO₂— | 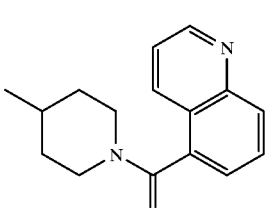 | —CH₃ | H. |

10. A pharmaceutical composition comprising an effective amount of a compound as defined in claim 1 in combination with a pharmaceutically acceptable carrier.

11. A method for treating Alzheimer's disease comprising administering to a patient suffering from said disease an effective amount of a compound of claim 1.

12. A method of treating Alzheimer's disease comprising administering to a patient suffering from said disease an effective amount of a combination of a compound of claim 1 with an acetyicholinesterase inhibitor.

13. A method of treating Alzheimer's disease comprising administering to a patient suffering from said disease an effective amount of a combination of an acetylcholine release enhancing compound of claim 1 with an acetylcholinesterase inhibitor.

14. The method of claim 13 wherein the acetylcholine release enhancing compound is an m2 selective muscarinic antagonist.

15. The method of claim 13 wherein the acetylcholine release enhancing compound is an m4 selective muscarinic antagonist.

16. A kit for treating Alzheimer's disease comprising in separate containers in a single package pharmaceutical compounds for use in combination, in one container a compound in accordance with claim 1 and in a separate container an acetylcholinesterase inhibitor, said compound and inhibitor each being in a pharmaceutically acceptable carrier and their combined quantities being an effective amount.

17. A kit for treating Alzheimer's disease comprising in separate containers in a single package pharmaceutical compounds for use in combination, in one container an acetylcholine release enhancing compound of claim 1 and in a separate container an acetylcholinesterase inhibitor, said compound and inhibitor each being in a pharmaceutically acceptable carrier and their combined quantities being an effective amount.

18. The kit of claim 17 wherein said acetylcholine release enhancing compound is an m2 selective muscarinic antagonist.

19. The kit of claim 17 wherein said acetylcholine release enhancing compound is an m4 selective muscarinic antagonist.

* * * * *